United States Patent [19]

Callne

[11] Patent Number: 5,076,786
[45] Date of Patent: Dec. 31, 1991

[54] CAST DENTAL MODEL ARTICULATOR SYSTEM AND METHOD

[76] Inventor: Lars E. Callne, 110 Los Patios, Los Gatos, Calif. 95030

[21] Appl. No.: 595,973

[22] Filed: Oct. 11, 1990

[51] Int. Cl.⁵ .............................................. A61C 11/00
[52] U.S. Cl. ...................................... 433/60; 433/65; 433/58
[58] Field of Search ........................ 433/65, 63, 60, 58

[56] References Cited

U.S. PATENT DOCUMENTS

| | | | |
|---|---|---|---|
| 1,654,453 | 12/1927 | Brown | 433/65 |
| 2,430,177 | 11/1947 | Johnson et al. | 423/65 |
| 2,600,899 | 6/1952 | McClain | 433/58 |
| 2,617,195 | 11/1952 | Perkell et al. | 433/65 |
| 3,409,986 | 11/1968 | Freeman | 433/58 |
| 3,510,947 | 5/1970 | Tuccillo et al. | 433/60 |
| 4,252,523 | 2/1981 | Gayso | 433/60 |
| 4,319,875 | 3/1982 | Beckwith | 433/60 |
| 4,412,822 | 11/1983 | Blechner | 433/60 |

*Primary Examiner*—John J. Wilson
*Attorney, Agent, or Firm*—Thomas E. Schatzel

[57] ABSTRACT

An articulator comprising two U-shaped wire frames joined by hinges and springs. The frames are snapped onto plastic clips cemented to dental casts. The clips allow the casts to be removed and reintroduced in repeatable positions. A slip-joint provides for left and right height adjustment between the dental casts to be adjusted or separated completely.

12 Claims, 4 Drawing Sheets

Fig_1 (Prior Art)

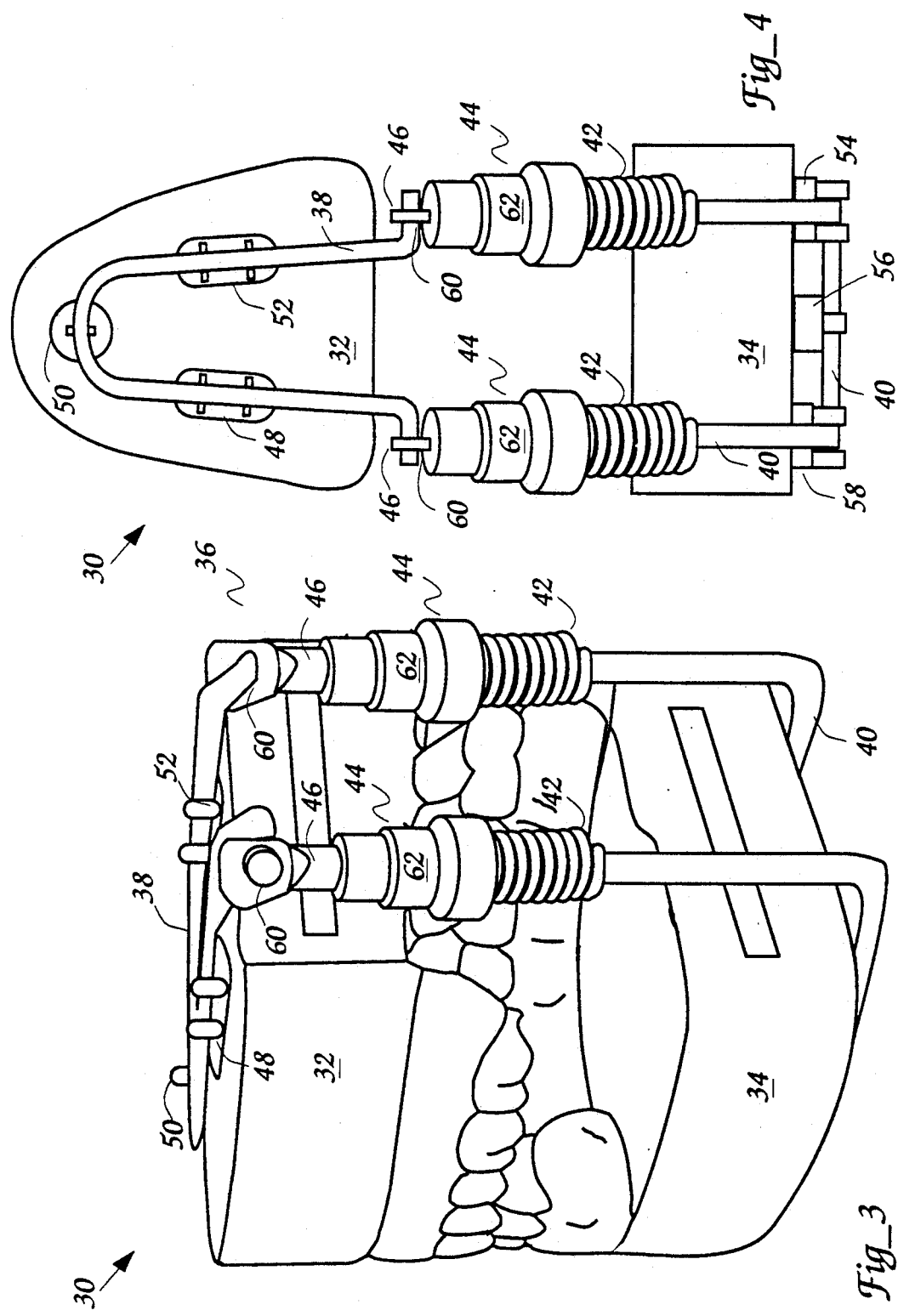

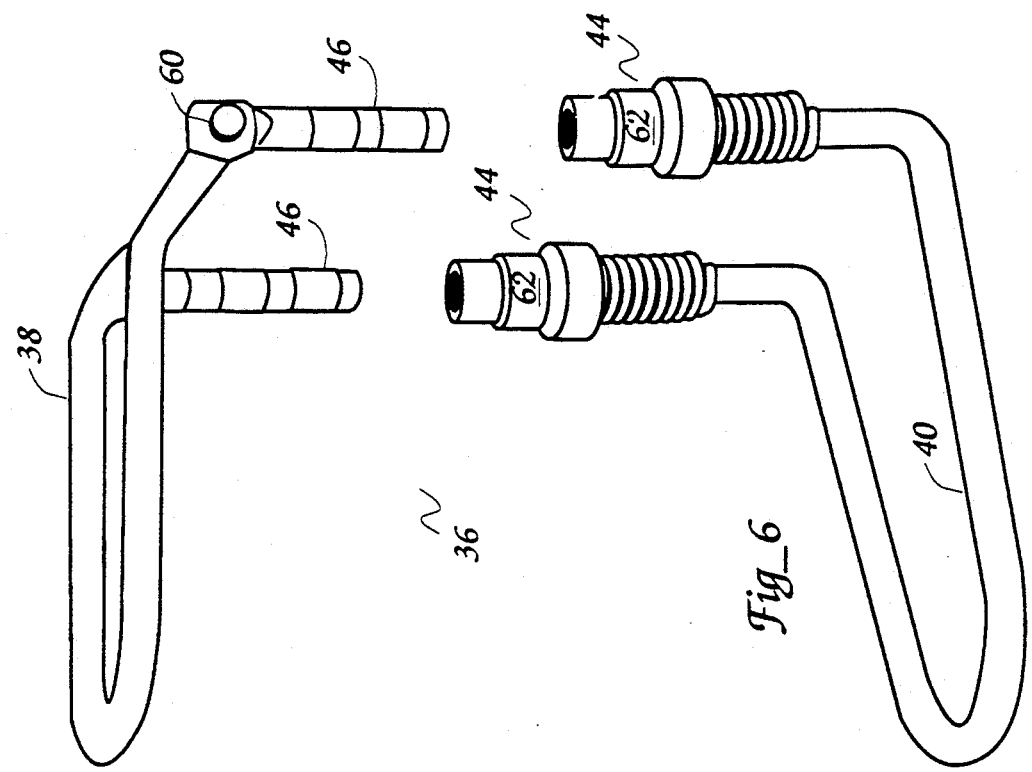
Fig_6
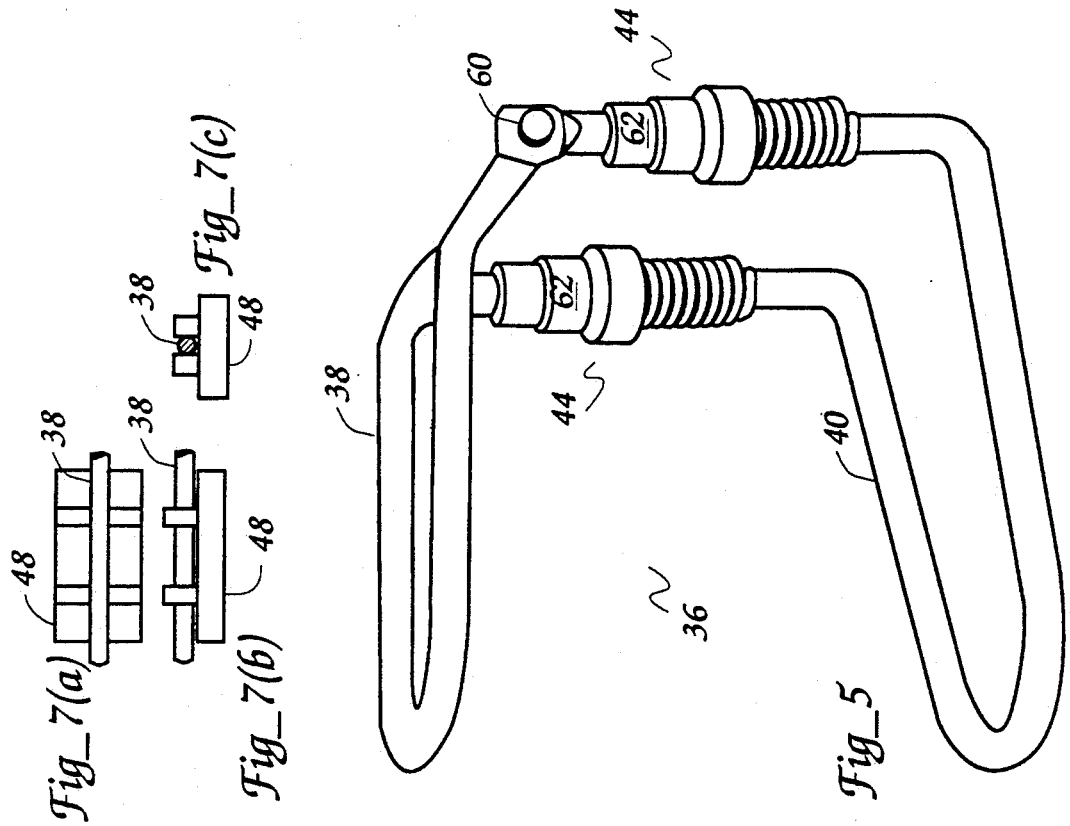
Fig_7(a)
Fig_7(b)
Fig_7(c)
Fig_5

CAST DENTAL MODEL ARTICULATOR SYSTEM AND METHOD

BACKGROUND OF THE INVENTION

1. Field of the Invention

The invention relates generally to dentistry and more specifically to articulators used with cast dental models that assist doctors and technicians in the construction of prosthetic dentures or denture elements by providing a model for fitting outside the patient's mouth.

2. Description of the Prior Art

Many different types of articulators have been commercially available for several years and are sold throughout the world. Articulators, or correlators as they are sometimes called, range from very simple to very complex devices. Disposable models exist as do models designed for re-use. Some articulators are capable of simulating the full range of occlusal and masticatory registrations observed in the patient population. A lack of such registration capabilities can often lead to inconveniencing the patient by requiring several visits for fitting. Simple articulators are easy to use but have a limited range of registrations. Complex articulators have a wide range of registrations, but are so difficult to use that formal training of the users is necessary. Either extreme results in higher costs for everyone involved.

Beyond simulating occlusal and masticatory registrations, an articulator should allow the inside area of the casts to be accessed. One way to do this is to hinge the upper cast to the lower cast FIGS. 1 shows a prior art method of doing this, that is disclosed in U.S. Pat. No. 4,382,787 issued May 10, 1983 to Huffman. FIG. 1 is an assembly, referred to by the general reference numeral 10, comprised of an upper cast 11, a lower cast 12, and an articulator 13. The articulator has a pair of mounts 14, a pair of ball joints 15, and a pair of hinges 16. The hinges 16 allow the distance between the mounts 14 on casts 11 and 12 to be adjusted. Articulator 13 is a disposable type, because ball joints 15 are intended to be adhesively locked after casts 11 and 12 are registered. Locking ball joints 15 prevents articulator 13 from being reused.

FIG. 2 is a prior art non-disposable articulator, referred to by the general reference numeral 20, and is similar to a type manufactured by Crescent Dental Manufacturing Company (Lyons, Ill.) under its "Flexi" trademark. Articulator 20 is a very simple device made of wire that has a pair of springs 22, a pair of hinges 24, an upper U-frame 26, and a lower U-frame 28. U-frames 26 and 28 are intended to be inserted into sockets in upper and lower dental casts (e.g., casts 12 and 14, respectively). The sockets are then plastered to retain articular 20. Articulator 20 cannot be removed from the casts without ruining the casts. Access to the inside area of the casts is possible by swinging upper U-frame 26 away from lower U-frame 28 on hinges 24. Articulator 20 does not allow a full range of registration, and the sockets in the casts intended to receive U-frames 26 and 28 must be precisely positioned. To remove articulator 20 from the casts, the casts probably will suffer some damage and this is certainly not a procedure that is likely to be attempted more than once.

A correlator similar to that of FIG. 2, but with several more complex features, is described in U.S. Pat. No. 2,430,177, issued Nov. 4, 1947, to Johnson, et al. A piano type hinge with an axle having the appearance of a cotter-pin joins two dental casts through four pins inserted into the casts, two in the upper cast and two in the lower cast. The cotter-pin axle allows the correlator to be separated by withdrawing the axle from the hinge, and it also allows the casts to be pivoted into an open position. Four wire helixes between each pin that enters into the casts and the hinge give some flexibility in the assembly. The correlator lacks a means to adjust the height of the upper cast to the lower cast and therefore makes the placement of where the pins enter the casts very critical. The method of holding the pins in, while removeable, is not as convenient, nor is it as easy to separate as the present invention, described below.

SUMMARY OF THE PRESENT INVENTION

It is therefore an object of the present invention to provide an articulator that has a wide range of registrations and is simple to use.

Briefly, a preferred embodiment of the present invention is an articulator comprising two U-shaped wire frames joined by hinges and springs. The frames are snapped onto plastic clips cemented to dental casts. The clips allow the casts to be removed and reintroduced in repeatable positions. A slip-joint provides for left and right height adjustment between the dental casts to be adjusted or separated completely.

An advantage of the present invention is that dental casts may be easily removed and re-attached to the articulator in a highly repeatable position.

These and other objects and advantages of the present invention will no doubt become obvious to those of ordinary skill in the art after having read the following detailed description of the preferred embodiments which are illustrated in the various drawing figures.

IN THE DRAWINGS

FIG. 3 is a perspective view of a preferred embodiment of an articulator of the present invention attached to two dental casts by clips attached to the upper and lower frames;

FIG. 4 is an end view of the articulator of FIG. 3 with the upper wire frame and dental cast raised up and vertical;

FIG. 5 is an elevational view of the articulator of FIG. 3 shown without the dental casts and clips;

FIG. 6 is an elevational view of the articulator of FIG. 5 showing how the dowels attached to the hinges on the upper frame separate from the compression nuts and sleeves on the lower frame; and FIG. 7(*a*) is a top view, FIG. 7(*b*) is a side view, and FIG. 7(*c*) is an end view of one of the clips shown in FIG. 4.

DETAILED DESCRIPTION OF THE PREFERRED EMBODIMENTS

Figure 1:
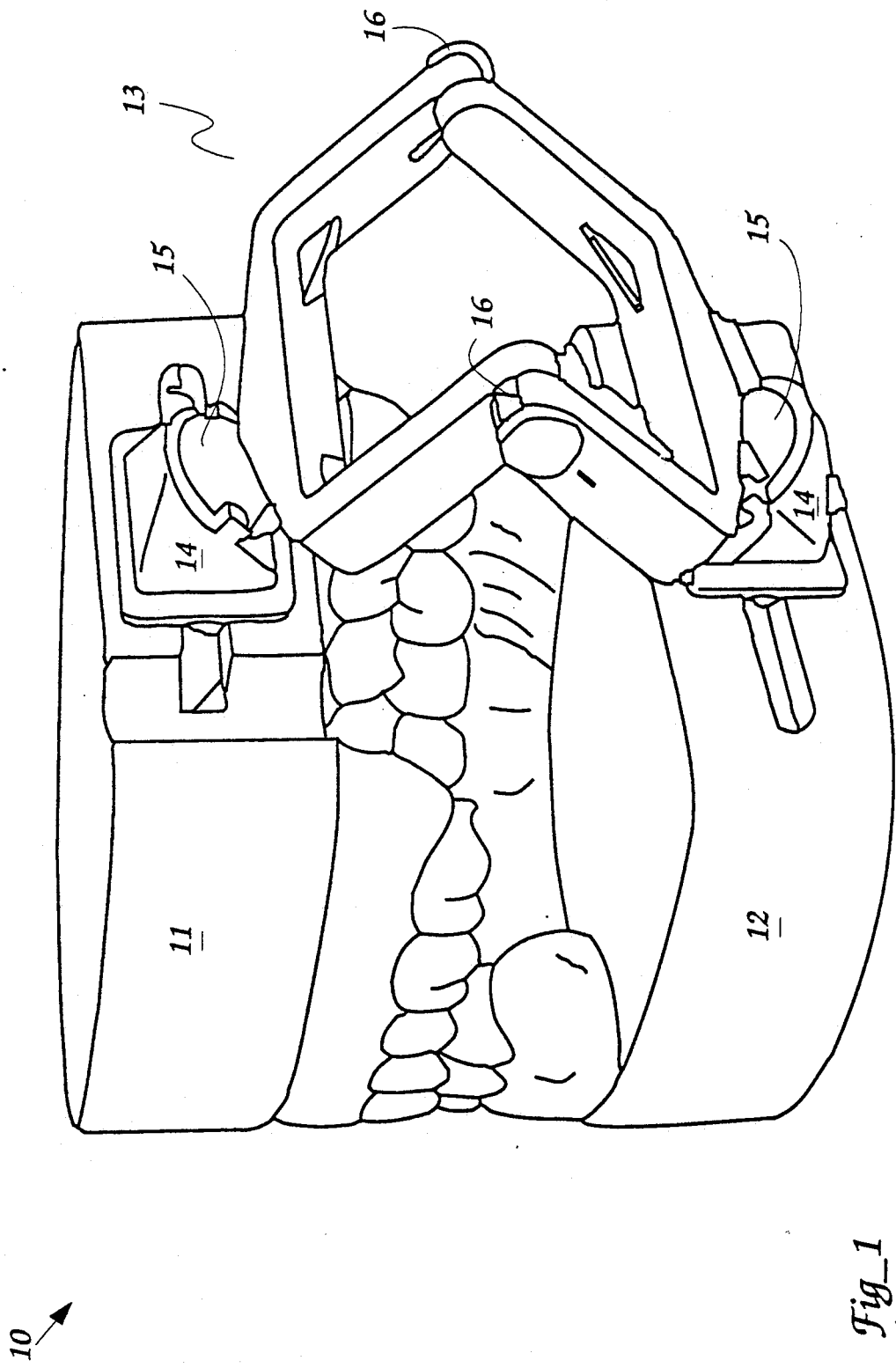
FIG. 1 is an elevational view of a prior art articulator attached to two dental casts.
Figure 2:
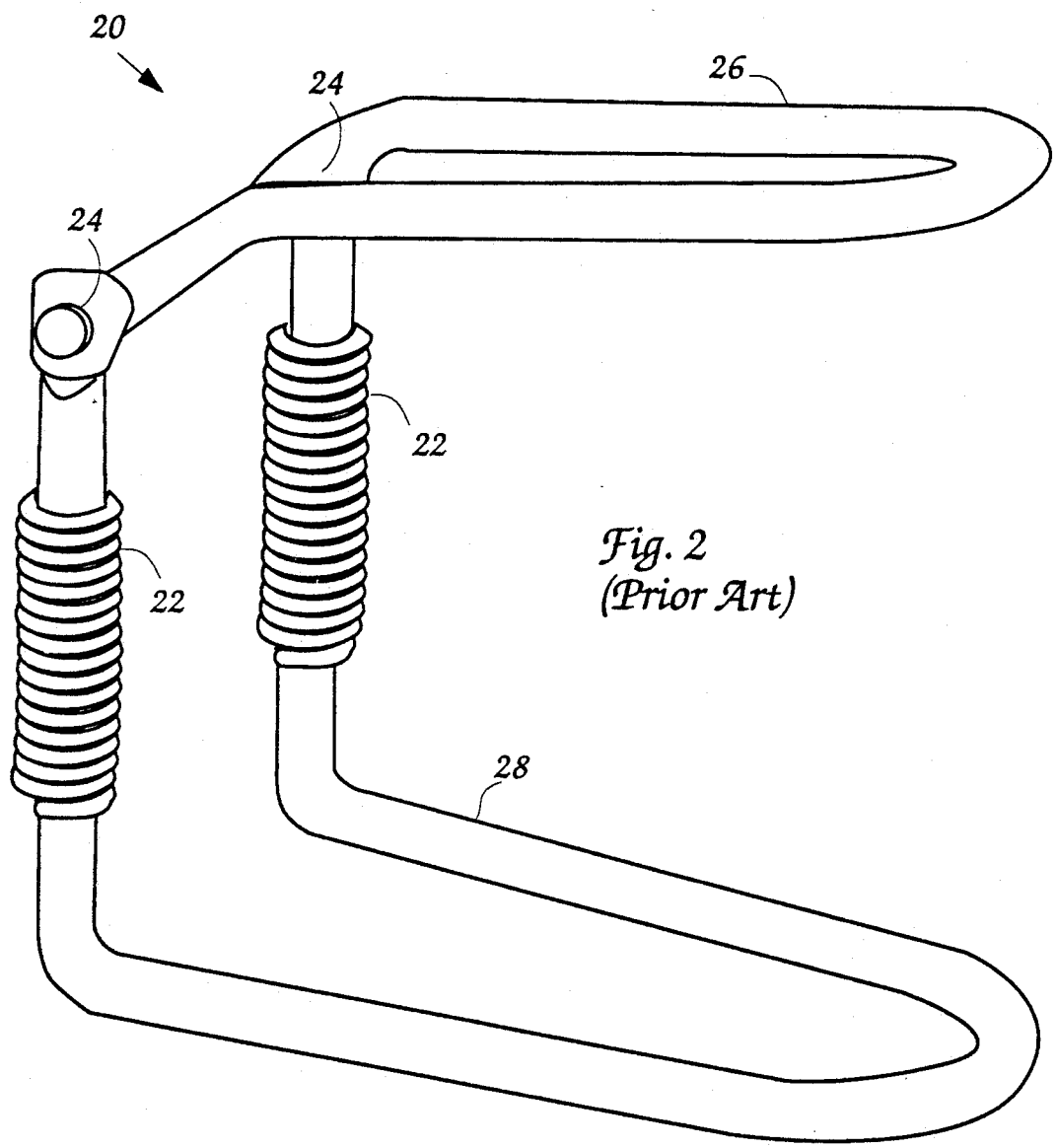
FIG. 2 is an elevational view of a prior art wire frame articulator.

FIG. 3 is an exemplary assembly, referred to by the general reference numeral 30, having an upper dental cast 32, a lower dental cast 34, and an articulator 36. The articulator 36 comprises an upper U-shaped frame 38, a lower U-shaped frame 40, a pair of springs 42, a pair of slip-joints 44, a pair of dowels 46, and clips 48, 50, 52, 54, 56, and 58. The upper and lower frames 38 and 40 are connected through a pair of hinges 60. The slip-joints 44 each have a compression sleeve (not shown) within a compression nut 62 that locks dowels 46 into their respective places. Slip-joints 44 allow dowels 46 to be individually locked into a number of positions. This allows both the height and the left-right tilt (referring to the view in FIG. 4) of hinges 60 to be adjusted in relation to frame 40.

FIG. 4 shows details and the attachment positions of clips 48, 50, 52, 54, 56, and 58. Clips 48, 52, 54, and 58 are oblong, while clips 50 and 56 are round. The oblong shape allows each clip to grasp frames 38 and 40 in two places. This will prevent horizontal twisting of dental casts 32 and 34. Other than that just described, the actual shapes of the clips are essentially immaterial. The U-bend in frame 38 in the exemplary embodiment is such that there would be little room for, e.g., clip 48 to replace clip 50. Three points of attachment are minimally preferred for frame 38 to cast 32 and for frame 40 to cast 34. Clips 48, 50, 52, 54, 56, and 58 are preferably made of plastic such that frames 38 and 40 will easily snap into them and will be held securely in place. Preferably, clips 48, 50, 52, 54, 56, and 58 are glued to casts 32 and 34 using a high strength adhesive. Alternatively, clips 48, 50, 52, 54, 56, and 58 could be screwed into casts 32 and 34, or attached by similar means. The attachment can be made any number of suitable ways, and the above means are only exemplary. In an alternative embodiment, clips 48, 50, and 52 are replaced by one very large plastic clip that snaps onto frame 38 in at least three places (to stabilize the plane of dental cast 32). Clips 54, 56, and 58 are also replaced by a very large plastic clip that snaps onto frame 40 in at least three places (to stabilize the plane of dental cast 34).

FIG. 5 is perspective view of articulator 36 without the clips and dental casts mounted to it. FIG. 6 shows how dowels 46 can be pulled completely out of slip-joints 44. Dowels 46 can also be locked in slip-joints 44 at various positions by tightening compression nut 62. Dowels 46 preferably have lateral grooves or ridges to help the locking action and the outside of slip-joints 44 are knurled to aid in hand tightening or loosening.

FIGS. 7(a-c) illustrate details of clip 48, and are also exemplary of clips 50, 52, 54, 56, and 58. A part of frame 38 snaps into clip 48. Frame 38 can be pried or twisted out of clip 48 and then later snapped back into place. Clip 48 is permanently secured to dental cast 32 and is disposable. Frame 38 is preferably plated with chrome or nickel. Alternatively stainless steel can be used. A smooth finish on frame 38 will help clip 48 snap on and off frame 38 easily.

Although the present invention has been described in terms of the presently preferred embodiments, it is to be understood that the disclosure is not to be interpreted as limiting. Various alterations and modifications will no doubt become apparent to those skilled in the art after having read the above disclosure. Accordingly, it is intended that the appended claims be interpreted as covering all alterations and modifications as fall within the true spirit and scope of the invention.

What is claimed is:

1. A plasterless articulator for registering an upper dental cast to a lower dental cast, comprising:
   an upper frame with left and right sides and a lower frame with left and right sides;
   at least one hinge member engaged to one of the frames such that one frame can be pivoted relative to the other frame;
   coupling means flexibly connecting the upper frame to the lower frame;
   disconnectable connection means joined to one of the frames for disengaging the upper and lower frames such that the upper and lower frames may be separated; and
   clips for securing directly to an upper dental cast and which snap onto the upper frame in a first position and for securing directly to a lower dental cast and which snap onto the lower frame in a second position, the clips being able to non-destructively release said upper dental cast and said lower dental cast from the upper and lower frames and able to directly recapture the upper and lower frames such that the clips and frames can be repeatedly separated but with the first and second positions substantially repeated upon securing the clips to the frames.

2. The articulator of claim 1, further comprising:
   right adjusting means coupled to the frames to adjust the relative distance between said right side of the upper frame and said right side of the lower frame; and
   left adjusting means coupled to the frames to adjust the relative distance between said left side of the upper frame and said left side of the lower frame.

3. The articulator of claim 2, wherein:
   the left and right adjusting means comprise a dowel that is inserted into a compression sleeve and nut, said dowel, sleeve, and nut connected to the respective frames.

4. The articulator of claim 1, wherein:
   said clips are made of plastic and are cemented onto the casts.

5. The articulator of claim 1, wherein:
   said clips are made of plastic and are screwed into the casts.

6. The articulator of claim 1, wherein:
   the coupling means comprises springs.

7. The articulator of claim 1, wherein:
   the disconnectible connection means comprise a dowel that is inserted into a compression sleeve and nut, said dowel, sleeve, and nut connected to the respective frames.

8. An improved wire frame dental cast articulator having upper and lower U-frames connected by hinges and springs, the improvement comprising:
   disconnection means for disengaging the upper frame from the lower frame;
   attachment means for securing directly to an upper dental cast and directly to the upper frame in a first position and for securing directly to a lower dental cast and directly to the lower frame in a second position, the attachment means being able to non-destructively release said upper dental cast and said lower dental cast from the upper and lower frames and able to directly recapture the upper and lower frames such that the attachment means and frames can be repeatably separated but with the first and second positions substantially repeated upon securing the attachment means to the frames;
   adjusting means to adjust the relative distance between said right side of the upper frame and said right side of the lower frame; and
   adjusting means to adjust the relative distance between said left side of the upper frame and said left side of the lower frame.

9. A plasterless method of dental cast articulation, comprising the steps of:

using an articular and engaging an upper frame to a lower frame of the articulator;

securing an upper dental cast directly to said upper frame in a first position by a first clip secured directly to said upper dental cast and frictionally engaged to said upper frame and directly securing a lower dental cast to said lower frame in a second position by a second clip secured directly to said upper dental cast and frictionally engaged to said lower frame, such that said upper and lower dental casts can be non-destructively released from said upper and lower frames and then recaptured in substantially said first and second positions.

10. The method of claim 9, wherein the articulator has an upper frame and a lower frame with left and right sides having at least one hinge between the frames, and further comprising the steps of:

engaging said upper frame to said lower frame with flexible means having a hinge;

adjusting the relative distance between said right side of the upper frame and said right side of the lower frame; and adjusting the relative distance between said left side of the upper frame and said left side of the lower frame.

11. The method of claim 10, wherein:

the securing is accomplished by adhering plastic molded clips to a surface of each dental cast opposite to the simulated teeth of the respective cast and snapping said clips to said respective frames.

12. The method of claim 10, wherein:

the adjustment of the relative distance is accomplished by adjusting a dowel that is disposed within a compression sleeve and nut, said dowel, sleeve, and nut connected to the respective frames.

* * * * *